US00PP10153P

United States Patent [19]

van Andel

[11] Patent Number: Plant 10,153

[45] Date of Patent: Dec. 16, 1997

[54] ALSTROEMERIA PLANT VARIETY NAMED 'STAKRIST'

[75] Inventor: Jacob van Andel, Aalsmeer, Netherlands

[73] Assignee: Van Staaveren b.v., Aalsmeer, Netherlands

[21] Appl. No.: 629,865

[22] Filed: Apr. 10, 1996

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 87T1558-01 and as pollen parent an unreleased, unpatented seedling identified as 87F1459-01 from among my collection of Alstroemeria seedlings maintained under controlled conditions in a greenhouse at Van Staaveren B.V., Aalsmeer, The Netherlands, for developmental purposes. The varietal denomination of the new variety is 'Stakrist'.

The first act of asexual reproduction of 'Stakrist' was in Aalsmeer, The Netherlands, by propagation by dividing rootstocks. Asexual reproduction through successive generations has demonstrated that the combination of characteristics as herein disclosed for 'Stakrist' are firmly fixed and retained through successive generations of asexual reproduction.

'Stakrist' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stakrist' are characterized by flowers of unusual coloration, as described herein. The plant blooms profusely with annual production, including production of flower stems in spring and fall under greenhouse conditions in The Netherlands, which is a desirable characteristic in a cut flower variety. The flower-bearing stems are of excellent quality. 'Stakrist' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:

*Family.*—Amaryllidaceae.

*Genus.*—Alstroemeria sp.

*Commercial.*—Alstroemeria hybrid.

Origin: Seedling.

PLANT

Form: Bush.

Shape: Upright.

Height: About 130 to 175 cm.

Growth rate: Medium.

Main stem or cane length: About 160 cm.

Growth: Vigorous.

Strength: Strong.

Foliage:

*Quantity.*—Abundant.

*Number of leaves.*—About 25 to 30 per stem.

*Size of leaf.*—Length: About 16 to 22 cm. Width: About 3 to 4 cm.

*Shape of leaf.*—Elliptical.

*Margin type.*—Straight.

*Texture.*—Glossy.

*Color.*—Upper side: Near 137A. Underside: Near 137C.

*Rhizomes.*—Yes Color: Near 155D. Size: About 10–30 cm.

INFLORESCENCE— FLOWER

Blooming habit: Recurrent.

Blooms: Profusely.

*Spring.*—Yes.

*Fall.*—Yes.

*Has tendency to give few blooms in fall.*—No.

Size: Medium

*Diameter.*—About 5 cm.

*Depth.*—About 5 cm.

Borne: Progressively along simple racemes.

Shape or form:

*When bloom first opens.*—Funnel form.

*When bloom matures.*—Funnel form.

Production: Good annual production, including production of flower stems in spring and fall under greenhouse conditions in The Netherlands.

Petalage:

*Number of petals.*—6.

*Arrangement.*—Two concentric circles of 3 petals.

*Form.*—Obovate.

*Margin type,*—Minutely crimped.

*Apex.*—Outer petals broadly cuspidate; green points, and, inner petals narrowly cuspidate with small, white, narrow points.

*How long do petals stay on stem?.*—About 3 weeks.

*Texture.*—Soft.

*Appearance.*—Velvety.

*Color (summer/fall).*—Outer petal/floret: Apical portions are red, near 39B which suffuses abruptly to a bright yellow, near 12A, which dominates the remainder of the surfaces of these petals; from about 40 to 50 stripes, near 187A, are presented in a pattern over the length of these petals; the color patterns and shadings of the reverse sides generally follow those of the top surface. Inside lateral petal: Body near 39B to near 12A; base near 39D; reverse side near 39B to near 12B; about 30 to 50 stripes, near 187A, per petal. Inside medial petal: Body near 39B to near 12A; base near 39D; reverse near 39B to 12B; about 40 to 50 stripes, near 187A.

Discoloration after full bloom? Slightly.

Is bloom affected by wet or hot weather? No.

Persistence (does flower hang on and dry?): No.

Disease resistance: Unknown.

Fragrance: None.

Lasting quality:

*On plant.*—About 3 weeks.

*As cut flower.*—About 14 days.

BUD

Size:

*Diameter.*—About 1 to 2 cm.

*Depth or length.*—About 2 to 3 cm.

Form or shape: Pear-shaped.

*Long.*—2 to 3 cm.

*Pointed.*—No.

Rate of opening: Fast.

Color of petals/florets

*When petals begin to unfurl.*—Near 39A.

REPRODUCTIVE ORGANS

Stamen:

*Number.*—6.

*Arrangement.*—Around the style.

Anthers:

*Size.*—About 6 to 8 mm.

*Color.*—Near 165B.

Filaments:

*Length.*—About 4 to 5 cm.

*Color.*—Near 39B.

Pollen:

*Color.*—Plan forms pollen that is moderate in quantity and light yellow, near 10B, in coloration.

Pistils

*Number.*—1.

Styles:

*Length.*—About 4 to 5 cm.

*Color.*—Near 39A to 39B.

Stigmas:

*Color.*—Near 39B.

FRUIT

Fertile: Yes.

Shape: Round.

Color at maturity: Near 163A.

I claim:

1. A new variety of Alstroemeria plant, substantially as herein shown and described.

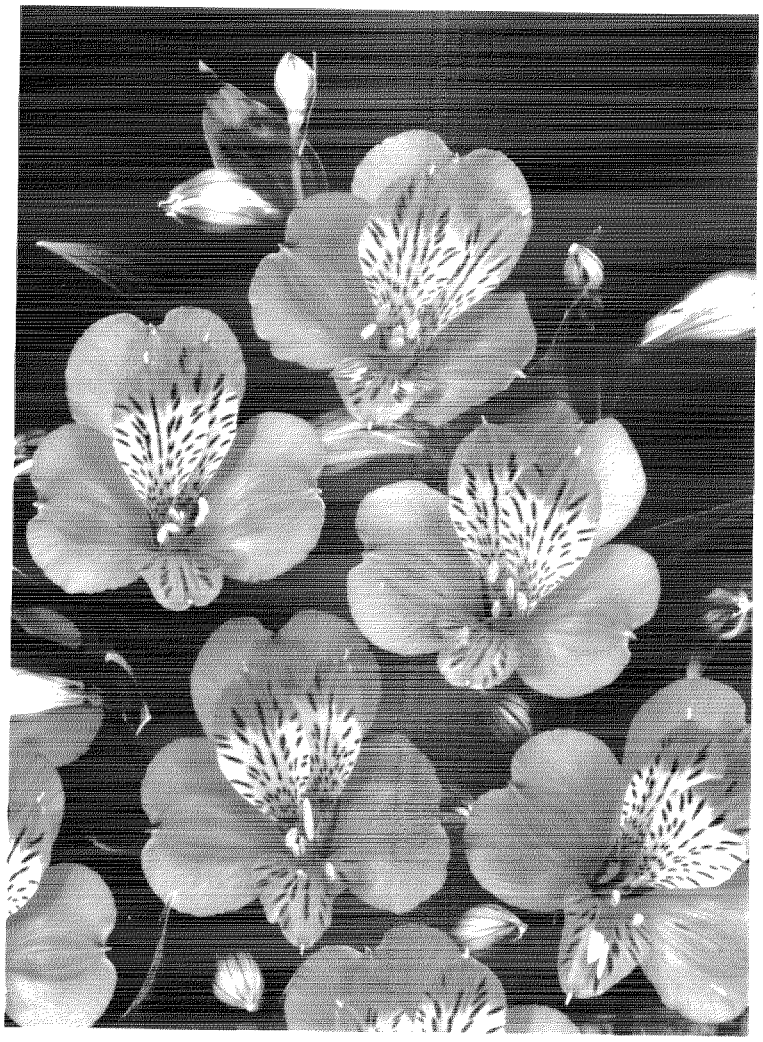

* * * * *